United States Patent
Kweeder et al.

(10) Patent No.: US 9,382,195 B2
(45) Date of Patent: Jul. 5, 2016

(54) OXIMATION OF KA OIL BY-PRODUCT

(71) Applicant: Honeywell International Inc., Morristown, NJ (US)

(72) Inventors: James A. Kweeder, Chesterfield, VA (US); Alan B Levy, Randolph, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 21 days.

(21) Appl. No.: 14/204,682

(22) Filed: Mar. 11, 2014

(65) Prior Publication Data
US 2014/0275627 A1    Sep. 18, 2014

Related U.S. Application Data

(60) Provisional application No. 61/784,106, filed on Mar. 14, 2013.

(51) Int. Cl.
*C07C 249/14* (2006.01)

(52) U.S. Cl.
CPC .................... *C07C 249/14* (2013.01)

(58) Field of Classification Search
None
See application file for complete search history.

(56) References Cited

U.S. PATENT DOCUMENTS

| | | | |
|---|---|---|---|
| 2,237,365 A | | 4/1941 | Schlack et al. |
| 2,552,513 A | * | 5/1951 | Blanchard et al. ............ 518/727 |
| 7,091,381 B2 | | 8/2006 | Suzuki et al. |
| 7,671,236 B2 | | 3/2010 | Hwang et al. |
| 2006/0194989 A1 | * | 8/2006 | Shirai .................. C07C 29/145 568/415 |

FOREIGN PATENT DOCUMENTS

| | | | |
|---|---|---|---|
| GB | 930842 | * | 7/1963 |
| WO | 2011003607 A2 | | 1/2011 |

OTHER PUBLICATIONS

PCT ISR & Written Opinion issued in PCT/US2014/023963 dated Jul. 30, 2014.
Yamamoto, Shigeru et al., Synthesis of ε-caprolactam precursors through the N-hydroxyphthalimide-catalyzed aerobic oxidation of K/A-oil, Green Chemistry, 2003, 5, pp. 300-302.

* cited by examiner

*Primary Examiner* — Sudhakar Katakam
*Assistant Examiner* — Jennifer C Sawyer
(74) *Attorney, Agent, or Firm* — Faegre Baker Daniels LLP

(57) ABSTRACT

The present disclosure provides methods for separating ketones and alcohols. In one embodiment, the methods and compositions disclosed are useful in separating cyclohexanol from cyclohexanone. In one embodiment, cyclohexanone is converted to its corresponding oxime by treating the cyclohexanone with hydroxylamine. The resulting cyclohexanone oxime is then separated from the cyclohexanol, providing streams of cyclohexanol and cyclohexanone oxime.

13 Claims, 6 Drawing Sheets

OXIMATION OF KA OIL BY-PRODUCT

CROSS-REFERENCE TO RELATED APPLICATIONS

This application claims the benefit under 35 U.S.C. §119(e) of U.S. Provisional Application Ser. No. 61/784,106, filed Mar. 14, 2013, the entire disclosure of which is hereby incorporated by reference in its entirety.

FIELD

The present invention relates to methods and apparatus for separating ketones and alcohols and, in particular, relates to methods and apparatus for separating cyclohexanone and cyclohexanol.

BACKGROUND

Cyclohexanone can be produced by the hydrogenation of phenol. Cyclohexanone is commonly used in the production of ε-caprolactam, which is a raw material used in the production of nylon 6. Nylon 6 has many uses including as a raw material used in industry and manufacturing.

The hydrogenation of phenol to cyclohexanone produces a small quantity of cyclohexanol as a by-product. The cyclohexanol is difficult to separate from cyclohexanone due to unfavorable relative volatilities in distillation, leaving a by-product stream of ketone/alcohol mixture ("KA oil") that is less desirable than its separated constituents.

Improvements in the foregoing processes are desired.

SUMMARY

The present disclosure provides methods for separating ketones and alcohols. In one embodiment, the methods and compositions disclosed are useful in separating cyclohexanol from cyclohexanone.

Because of the unfavorable relative volatilities, it is difficult to separate cyclohexanol and cyclohexanone from a mixture using traditional distillation techniques. However, treating a mixture of cyclohexanol and cyclohexanone with hydroxylamine results in the cyclohexanone being converted into cyclohexanone oxime. Cyclohexanone oxime can be more easily separated from cyclohexanol than cyclohexanone. This facilitates the separation of a mixture of cyclohexanone and cyclohexanol into a stream of cyclohexanol, which can be purified for sale or further use, e.g. as a solvent, and a stream of cyclohexanone oxime, which can be further converted to caprolactam through a Beckmann rearrangement reaction.

In one exemplary embodiment, a process for separating an alcohol from a ketone/alcohol mixture is provided. The method comprises providing a first stream comprising a ketone and an alcohol; adding a reagent to the first stream, said reagent reacting with the ketone to form an oxime, wherein the oxime has low solubility in the alcohol; and separating the oxime and alcohol.

The above mentioned and other features of the invention, and the manner of attaining them, will become more apparent and the invention itself will be better understood by reference to the following description of embodiments of the invention taken in conjunction with the accompanying drawings.

DETAILED DESCRIPTION

Although not so limited, the separation process described herein is particularly useful separating a cyclohexanol product from cyclohexanone produced from the hydrogenation of phenol.

Figure 1A:
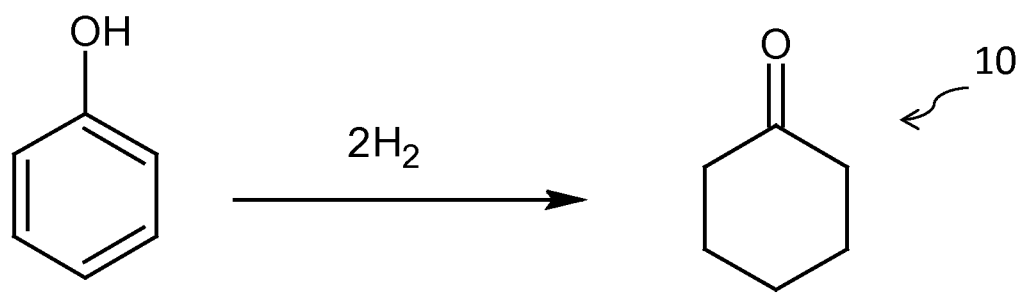
FIG. 1A illustrates the hydrogenation of phenol to form cyclohexanone.
Figure 1B:
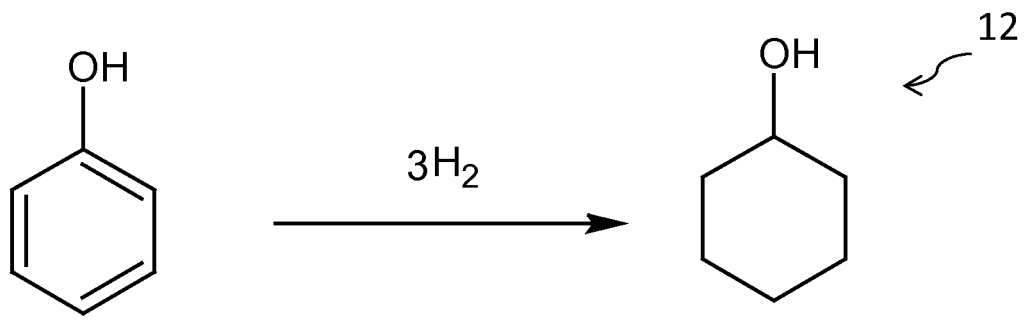
FIG. 1B illustrates the hydrogenation of phenol to form cyclohexanol.

As illustrated by the reaction 10 in FIG. 1A, phenol can be hydrogenated in the presence of a catalyst, to form cyclohexanone. Exemplary catalysts include palladium, platinum, ruthenium, and other suitable catalysts. However, a portion of the phenol is hydrogenated to form cyclohexanol according to reaction 12 in FIG. 1B.

Figure 2:
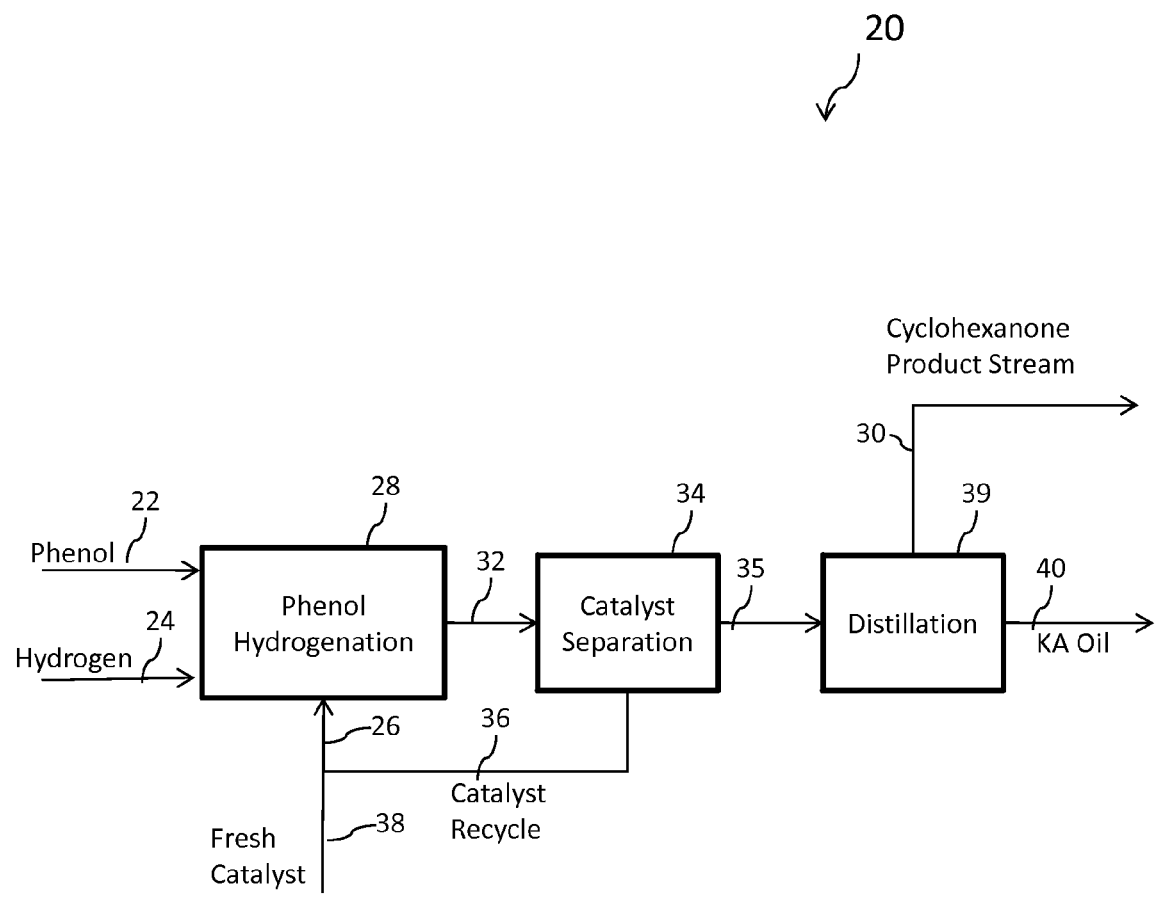
FIG. 2 illustrates a schematic of an exemplary phenol hydrogenation process producing a KA oil product stream.

Referring next to FIG. 2, a generalized phenol hydrogenation process 20 is shown. Phenol 22 and hydrogen 24 are reacted in the presence of a metal catalyst 26 in phenol hydrogenation step or unit 28, forming cyclohexanone and cyclohexanol. Exemplary metal catalysts include palladium, platinum, ruthenium, and other suitable catalysts. Catalyst is separated from the cyclohexanone and cyclohexanol mixture 32 in catalyst separation step or unit 34 and recycled 36 back to the hydrogenation step or unit 28. Additional fresh catalyst 38 may be added to maintain the level of catalyst in hydrogenation step or unit 28.

The cyclohexanone and cyclohexanol stream 35 is then distilled in distillation step or unit 39. A first portion of the cyclohexanone product stream is removed, as illustrated by cyclohexanone product stream 30, while a second portion of the cyclohexanone and the cyclohexanol remain in a mixture as KA oil stream 40. Any residual phenol may be stripped from stream 35 in an additional process (not shown).

In one embodiment, the KA oil has a ratio of the weight of cyclohexanone to the weight of cyclohexanol as little as 0.1:1, 0.5:1, 0.75:1, 0.9:1, 0.95:1, 1:1, as great as 1.05:1, 1.1:1, 1.25:1, 2:1, 3:1, 5:1, 10:1, 20:1, or within any range defined between any pair of the foregoing values.

The KA oil product stream 40 may be further processed to form additional products, such as adipic acid. However, it is desirable to further separate the ketone and alcohol constituents of the KA oil product stream.

Figure 3:
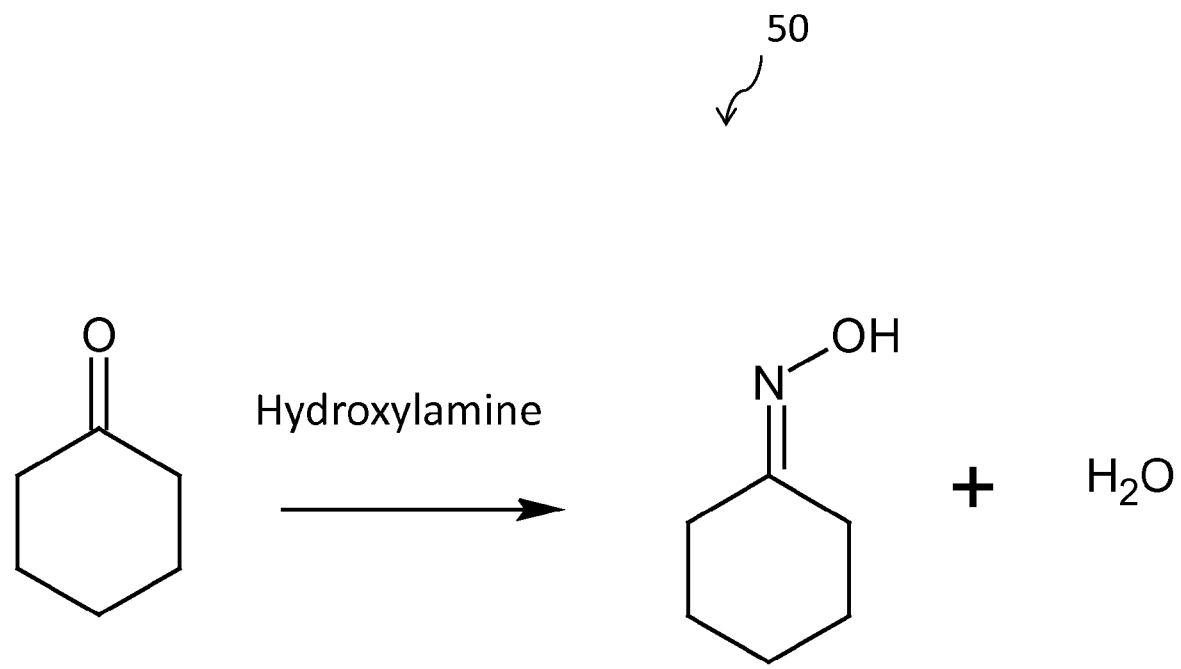
FIG. 3 illustrates the oximation of cyclohexanone by hydroxylamine to form cyclohexanone oxime.

The cyclohexanol is difficult to separate from cyclohexanone due to unfavorable relative volatilities in distillation. However, as illustrated in FIG. 3, cyclohexanone can be reacted with hydroxylamine ($NH_2OH$) in oximation reaction 50 to form cyclohexanone oxime. Illustratively, hydroxylamine may be provided as a salt of hydroxylamine, or as hydroxylamine free base. Exemplary salts of hydroxylamine include hydroxylamine sulfate, hydroxylamine chloride, hydroxylamine fluoride, hydroxylamine nitrate, and other suitable salts. An exemplary free base form of hydroxylamine is provided as an aqueous solution or as a solution with another solvent. Exemplary aqueous solutions include concentrated solutions, diluted concentrations, and solutions with a concentration of hydroxylamine of about 50 wt. % or less.

Figure 4A:
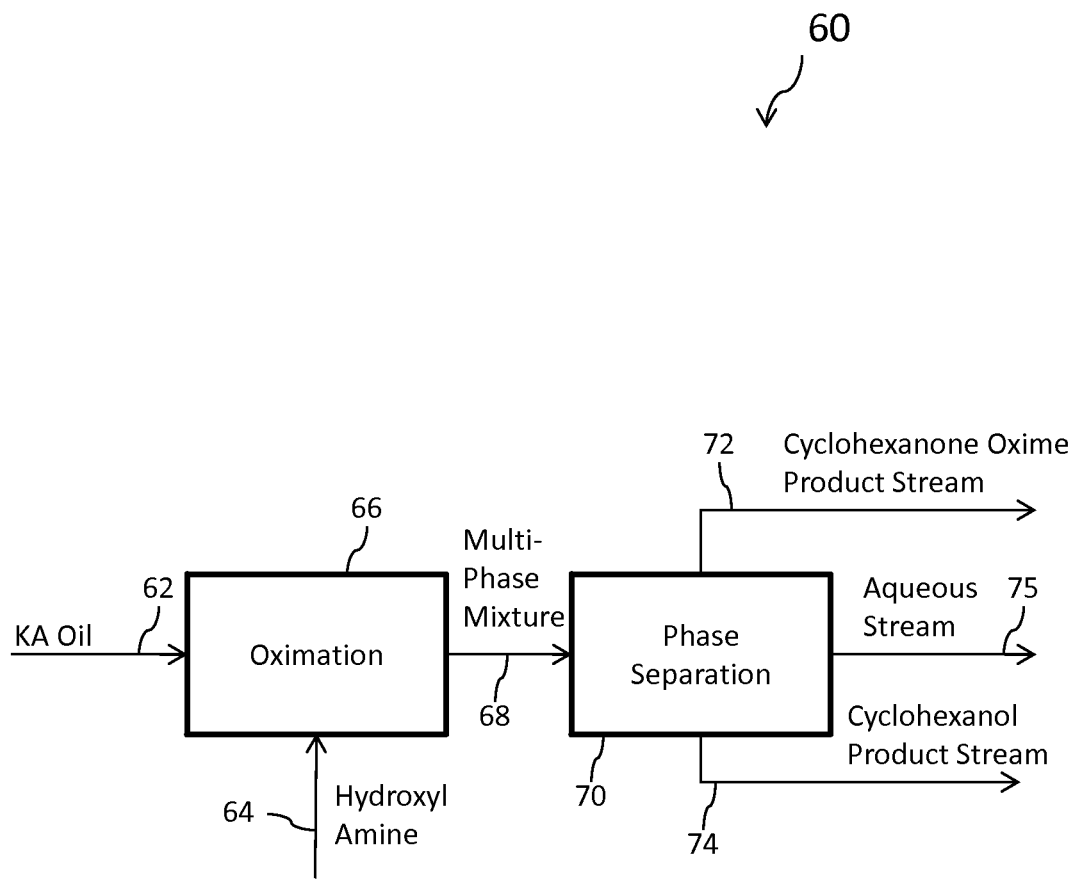
FIG. 4A illustrates a schematic of an exemplary oximation and separation process for KA oil using hydroxyl amine according to the present disclosure.

Referring next to FIG. 4A, a generalized oximation process 60 is shown. KA oil 62 is provided. In one embodiment, KA oil 62 is the same as KA oil stream 40 from phenol hydrogenation process 20 (see FIG. 2).

Hydroxylamine 64 is added to the KA oil 62 in oximation step or unit 66. In an exemplary embodiment, oximation step or unit 66 may include a reactor having a stirred batch reactor, continuous stirred tank reactor, back mixed reactor, or plug-flow reactor design. Other suitable reactors may also be used. In an exemplary embodiment, the amount of hydroxylamine added to the KA oil is a stoichiometric amount of hydroxylamine based on the amount of ketone in the KA oil. In other embodiments, the amount of hydroxyl amine may be as little as 10% less, 5% less, 2% less, 1% less, as great as 1% excess, 2% excess, 5% excess, 10% excess of the stoichiometric amount based on the amount of ketone in the KA oil.

Oximation step or unit 66 results in the cyclohexanone reacting with the hydroxylamine to form cyclohexanone oxime. Unlike cyclohexanone which is soluble in cyclohexanol, cyclohexanone oxime is not highly soluble in cyclohexanol. The low solubility provides a multi-phase mixture 68 of cyclohexanone oxime, cyclohexanol that facilitates easier separation compared to the cyclohexanone and cyclohexanol. In some embodiments, multi-phase mixture 68 further includes an aqueous phase. The multi-phase mixture 68 is separated in phase separation step or unit 70 to produce cyclohexanone oxime product stream 72, cyclohexanol product stream 74, and, in some embodiments, aqueous stream 75.

Phase separation step or unit 70 may consist of a single phase separation process or multiple processes. Exemplary methods of separating the cyclohexanone oxime and cyclohexanol in phase separation step or unit 70 include physical separation methods such as filtration, centrifugation, decantation, flash distillation, thermal separation methods, such as distillation, and/or extraction methods which utilize the different solubility characteristics of oximes and cyclic alcohols.

Figure 4B:
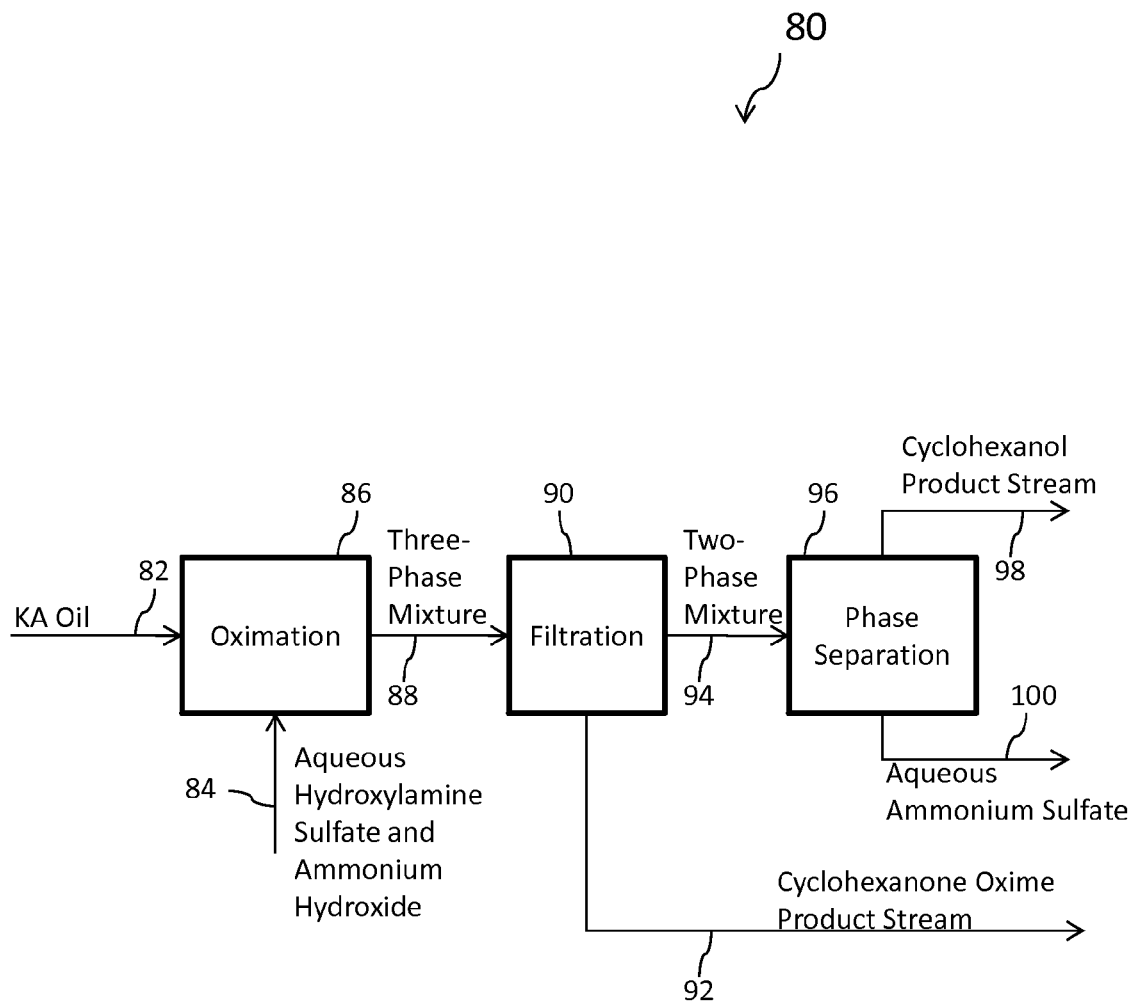
FIG. 4B illustrates a schematic of another exemplary oximation and separation process for KA oil using a salt of hydroxyl amine according to the present disclosure.

Referring next to FIG. 4B, another generalized oximation process 80 is shown. KA oil 82 is provided. In one embodiment, KA oil 82 is the same as KA oil stream 40 from phenol hydrogenation process 20 (see FIG. 2).

An aqueous solution of hydroxylamine sulfate 84 is added to the KA oil 82 in oximation step or unit 86. The aqueous solution of hydroxylamine sulfate illustratively includes ammonia or ammonium hydroxide. In a more particular illustrative embodiment, the aqueous solution of hydroxylamine sulfate includes an equimolar amount of ammonia or ammonium hydroxide on a hydroxyl amine basis, or two molar equivalents ammonia on a hydroxyl amine sulfate basis. In an exemplary embodiment, the amount of hydroxylamine added to the KA oil as hydroxylamine sulfate is a stoichiometric amount of hydroxylamine based on the amount of ketone in the KA oil. In other embodiments, the amount of hydroxyl amine may be as little as 10% less, 5% less, 2% less, 1% less, as great as 1% excess, 2% excess, 5% excess, 10% excess of the stoichiometric amount based on the amount of ketone in the KA oil.

Oximation step or unit 86 results in the cyclohexanone reacting with the hydroxylamine sulfate to form cyclohexanone oxime. The cyclohexanone oxime is sparingly soluble in either the cyclohexanol or the aqueous phase, resulting in the cyclohexanone oxime being present as a solid precipitate in stream 88 when the cyclohexanone oxime is at a temperature below its melt point, illustratively about 88-91° C. in one embodiment, or about 85-91° C. in another embodiment.

The cyclohexanone oxime is removed from the cyclohexanol and aqueous phase by filtration or other suitable physical separation method in filtration step or unit 90.

The resulting two phase mixture 94 following filtration step or unit 90 is separated in phase separation step or unit 96 to produce a crude cyclohexanol product stream 98 and an aqueous ammonium sulfate product stream 100.

Exemplary methods of separating the cyclohexanol and aqueous phase in separation step or unit 96 include physical separation methods such as phase separation, filtration, centrifugation, decantation, and other suitable methods.

Referring next to FIGS. 4A and 4B, once separated, the cyclohexanone oxime product streams 72, 92 are crude product streams that can be further purified by methods such as filtering and drying, flashing, evaporation, or flashing in a wiped film evaporator. The separated cyclohexanol product streams 74, 98 are crude product streams can be purified for sale or for further use. The aqueous ammonium sulfate stream 100 can be further purified for sale or further use, such as for a fertilizer or fertilizer production process.

Figure 4C:
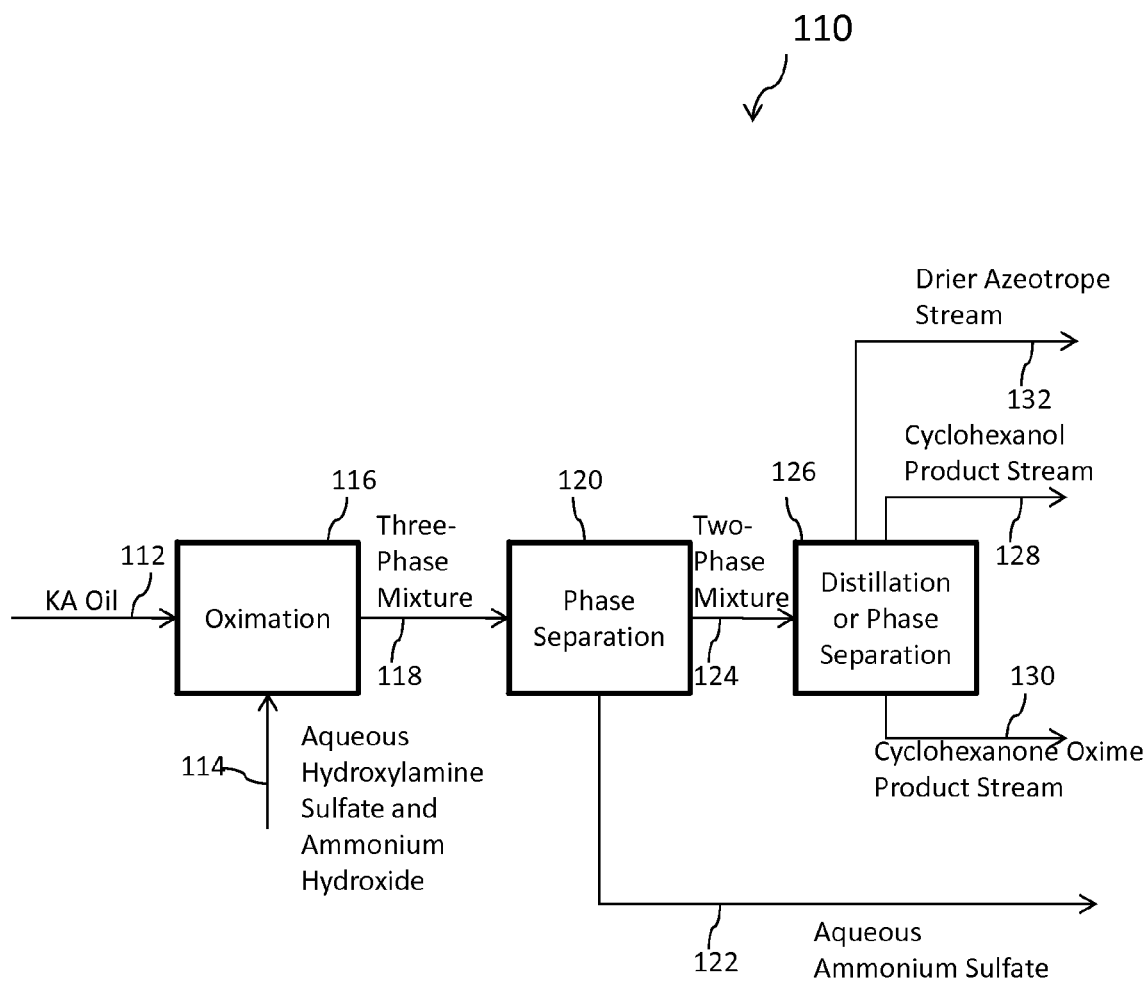
FIG. 4C illustrates a schematic of still another exemplary oximation and separation process for using KA oil using a salt of hydroxyl amine.

Referring next to FIG. 4C, still another generalized oximation process 110 is shown. KA oil 112 is provided. In one embodiment, KA oil 112 is the same as KA oil stream 40 from phenol hydrogenation process 20 (see FIG. 2).

An aqueous solution of hydroxylamine sulfate 114 is added to the KA oil 112 in oximation step or unit 116. The aqueous solution of hydroxylamine sulfate illustratively includes ammonia or ammonium hydroxide. In a more particular illustrative embodiment, the aqueous solution of hydroxylamine sulfate includes an equimolar amount of ammonia or ammonium hydroxide on a hydroxyl amine basis, or two molar equivalents ammonia on a hydroxyl amine sulfate basis. In an exemplary embodiment, the amount of hydroxylamine added to the KA oil as a salt is a stoichiometric amount of hydroxylamine based on the amount of ketone in the KA oil. In other embodiments, the amount of hydroxyl amine may be as little as 10% less, 5% less, 2% less, 1% less, as great as 1% excess, 2% excess, 5% excess, 10% excess of the stoichiometric amount based on the amount of ketone in the KA oil.

Oximation step or unit 116 results in the cyclohexanone reacting with the hydroxylamine sulfate to form cyclohexanone oxime. The cyclohexanone oxime is sparingly soluble in either the cyclohexanol or the aqueous phase, resulting in the cyclohexanone oxime being present as an oil in stream 118 when the cyclohexanone oxime is at a temperature above its melt point, illustratively about 88-91° C.

The resulting three phase mixture stream 118 is separated in phase separation step or unit 120 to produce a crude aqueous ammonium sulfate product stream 122 and two-phase mixture 124 of cyclohexanol and cyclohexanone oxime. Exemplary methods of separating the aqueous phase in separation step or unit 96 include physical separation methods such as phase separation, filtration, centrifugation, decantation, flash distillation, thermal separation methods, such as distillation, and/or extraction methods which utilize the different solubility characteristics of oximes and cyclic alcohols.

The two-phase mixture 124 of cyclohexanone oxime and cyclohexanol is separated in distillation or phase separation step or unit 126 to produce a crude cyclohexanol product stream 128 and crude cyclohexanone oxime product stream 130.

In one embodiment, the two phase mixture 124 contains less than about 5% water, with the balance being a mixture of cyclohexanol and cyclohexanone oxime. Distillation or phase separation step or unit 126 illustratively includes a drier for removing the water as an azeotrope of water and cyclohexanone, shown as drier azeotrope stream 132. Distillation or phase separation step or unit 126 further includes a wiped film evaporator which removes the cyclohexanol overhead under vacuum conditions as the cyclohexanol product stream 128. In some embodiments, the bottoms temperature of the wiped film evaporator is maintained at a temperature as low as 130° C., 120° C., 110° C., or lower, or within any range defined between any two of the foregoing values.

Once separated, the cyclohexanone oxime product stream 130 is a crude product streams that can be further purified such by filtering and drying, flashing, evaporation, or flashing in a wiped film evaporator. In some embodiments, cyclohexanone oxime product stream 130 includes residual cyclohexanol as low as 20 wt. %, as low as 2 wt. %, as low as 0.2 wt. %, or lower, or within any range defined between any two of the foregoing values. In some embodiments, cyclohexanone oxime product stream 130 can be used either alone or mixed with a more pure cyclohexanone oxime stream in a Beckmann rearrangement reaction to produce caprolactam. The separated cyclohexanol product stream 128 is a crude product stream that can be purified for sale or for further use. The aqueous ammonium sulfate stream 122 can be further purified for sale or further use, such as for a fertilizer or fertilizer production process.

While the present disclosure is primarily directed to separating a cyclohexanone and cyclohexanol produced from the hydrogenation of phenol, it should be understood that the features disclosed herein may have application to other mixtures containing ketones, other ketone and alcohol separations, and to ketones and alcohols from other sources.

While this invention has been described as relative to exemplary designs, the present invention may be further modified within the spirit and scope of this disclosure. Further, this application is intended to cover such departures from the present disclosure as come within known or customary practice in the art to which this invention pertains.

What is claimed is:

1. A process for separating an alcohol from a ketone/alcohol mixture comprising the steps of:
    reacting phenol with hydrogen to produce a first stream comprising cyclohexanone and cyclohexanol, wherein the first stream has a ratio of the weight of cyclohexanone to the weight of cyclohexanol from 0.5:1 to 1.25:1;
    adding a reagent to the first stream, wherein the reagent is selected from hydroxylamine free base and a salt of hydroxylamine, said reagent reacting with cyclohexanone to form cyclohexanone oxime; and
    separating the cyclohexanone oxime and the cyclohexanol.

2. The process of claim 1, wherein the reagent is provided as an aqueous solution including hydroxylamine free base.

3. The process of claim 1, wherein said adding step further comprises adding a stoichiometric amount of the reagent based on the amount of cyclohexanone in the first stream.

4. The process of claim 1, wherein said adding step further comprises adding an amount of the reagent from 10% less than to 10% in excess of the stoichiometric amount based on the amount of cyclohexanone in the first stream.

5. The process of claim 1, wherein said separating step further includes a separation method selected from the group consisting of flash distillation, thermal distillation, filtration, centrifugation, decantation, phase separation, and solvent extraction.

6. The process of claim 1, wherein the reagent is a salt of hydroxylamine.

7. The process of claim 6, where the salt of hydroxylamine is selected from the group consisting of hydroxylamine sulfate, hydroxylamine nitrate, hydroxylamine chloride, and hydroxylamine fluoride.

8. The process of claim 6, wherein said adding step further comprises adding an aqueous solution comprising the salt of hydroxylamine to the first stream.

9. A process for separating an alcohol from a ketone/alcohol mixture comprising the steps of:
    providing a first stream comprising cyclohexanone and cyclohexanol wherein the first stream has a ratio of the weight of cyclohexanone to the weight of cyclohexanol from 0.5:1 to 1.25:1;
    adding an aqueous solution of a salt of hydroxyl amine and ammonia or ammonium hydroxide to the first stream to form a three-phase mixture comprising cyclohexanone oxime, cyclohexanol, and aqueous ammonium sulfate; and
    separating the three-phase mixture to form a cyclohexanone oxime product stream, a cyclohexanol product stream, and an aqueous ammonium sulfate product stream.

10. The process of claim 9, wherein said separating step further includes a separation method selected from the group consisting of phase separation, filtration and centrifugation.

11. The process of claim 10, further comprising the step of separating the cyclohexanol and ammonium sulfate by at least one separation method selected from the group consisting of flash distillation, thermal distillation, centrifugation, and decantation.

12. The process of claim 9, wherein said separating step comprises:
    filtering the cyclohexanone from the three-phase mixture to form a two-phase mixture of cyclohexanol and aqueous ammonium sulfate; and
    separating the two-phase mixture to form a cyclohexanol product stream and an aqueous ammonium sulfate product stream.

13. The process of claim 9, wherein said separating step comprises:
    separating the three-phase mixture into an aqueous ammonium sulfate product stream and a two-phase mixture of cyclohexanol and cyclohexanone oxime; and
    separating the two-phase mixture to form a cyclohexanol product stream and a cyclohexanone oxime product stream.

\* \* \* \* \*